United States Patent [19]

Bogert

[11] 4,137,918
[45] Feb. 6, 1979

[54] MEDICAL BY-PASS DEVICE FOR USE AFTER OSTOMY SURGERY

[76] Inventor: Clayton Bogert, 118 Lowell Rd., Glenrock, N.J. 07452

[21] Appl. No.: 800,677

[22] Filed: May 26, 1977

Related U.S. Application Data

[63] Continuation of Ser. No. 642,211, Dec. 18, 1975, abandoned.

[51] Int. Cl.² .............................................. A61F 5/44
[52] U.S. Cl. .................................................. 128/283
[58] Field of Search ............... 128/283, 351, 239, 240, 128/232, 127, 128, 130, 131; 3/1, 1.3

[56] References Cited

U.S. PATENT DOCUMENTS

| 3,144,866 | 8/1964 | Ellis | 128/232 |
| 3,439,679 | 4/1969 | Doolittle | 128/283 |
| 3,802,435 | 4/1974 | Claasen | 128/232 |

OTHER PUBLICATIONS

Clay–Adams Catalog, p. 144, N.Y., N. Y., 1953, Gelchorn Pessaries.

Primary Examiner—Robert W. Michell
Assistant Examiner—Henry S. Layton
Attorney, Agent, or Firm—Arthur A. March

[57] ABSTRACT

A device for insertion in a surgically created orifice after ostomy surgery to provide a tube or flow path for the excretion of body wastes from the body organ. There is an enlarged base portion, a tapered portion adjacent thereto and an integral substantially cylindrical portion extending from the tapered portion. The device terminates in an enlarged flared tip or shoulder which is inserted into the orifice in the skin. The enlarged tip or shoulder is larger in diameter than the diameter of the orifice whereby when the shoulder is inserted the ureter, colon or ileum, as the case may be, will enwrap the shoulder and maintain the device in secured position. A disposable bag is provided to be applied to the base portion of the by-pass device.

3 Claims, 5 Drawing Figures

MEDICAL BY-PASS DEVICE FOR USE AFTER OSTOMY SURGERY

This is a continuation, of application Ser. No. 642,211 filed on Dec. 18, 1975, now abandoned.

BACKGROUND OF THE INVENTION

Ostomy surgery results in the provision of a surgically created orifice in the body which extends to or from an organ to by-pass the normal channels used for the excretion of body wastes. Examples of this type of surgery are commonly referred to as Urostomy, Ureterostomy, Colostomy and Ileostomy.

In order to accumulate and contain the body wastes, presently used devices consist, for the most part, of bag-like means which are attached around the stoma by means of an adhesive or by straps fastening around the body. Both of these presently known devices present many serious problems. For example, where adhesive devices are used, particularly after a Urostomy or Ureterostomy, there are a great many difficulties. This type of operation requires an artificial collection and elimination of kidney wastes and it is very difficult under such conditions to maintain the area around the stoma or opening in a completely dry state while the adhesive is being applied. Further, it is necessary to prevent the adhesive from in any way contacting the stoma or opening with the consequent bacteriological and other harmful results. It also will be realized that keeping the area dry where the adhesive is applied is quite a problem because of the constant discharge of the body waste. In some instances it has been suggested that the collection device be provided with a pre-applied adhesive but in this situation also the skin area surrounding the stoma or opening must be completely dry and the adherence and adhesive quality of such pre-applied adhesive devices is far from satisfactory. Furthermore, even in this instance, the collection of body waste at the point of adhesion weakens the adherence which when combined with the normal movement of the body breaks down the liquid tight seal and permits the body waste to leak. The second requirement for the removal of the old adhesive and reapplication of fresh adhesive tends to break down the skin tissue over a period of time.

In addition to the adhesive devices set forth above, proposals have been made for devices which are attached to the body by straps or the like, particularly in the case of the presentation of an artificial opening after a colostomy or ileostomy. Such devices, however, do not and cannot provide an air-tight seal and from time to time the waste material itself comes in contact with the skin which in certain instances, particularly after an ileostomy, results in the breakdown of skin tissues.

In addition to the foregoing problems, because of the constant need to tend the adhesively-applied devices as well as those applied with strap-on means, it has been difficult for the wearer to pursue the normal everyday functions requiring freedom of movement of the body. In fact, the person using such devices is quite incapacitated by the great necessity for care and constant attendance thereon, as well as the dangers prevalent due to leakage and the like.

SUMMARY OF THE INVENTION

The present invention eliminates the foregoing problems and presents a new and novel device for use after ostomy surgery which does not require any adhesive or strap members in order to secure it to the body. Further, a substantially airtight seal is provided whereby leakage and other problems are eliminated. In addition, there are no harmful or toxic substances utilized which thereby prevents any injury to the skin.

To accomplish this beneficial result, the invention provides a relatively simple unit comprising a tubular member, one end of which may be inserted directly into the surgically created orifice through which the waste material can pass into a bag attached to the other end of the device. This unique and novel device has a relatively enlarged base portion from which a tapering portion extends. The tapering portion terminates in a relatively cylindrical section. A flaring enlarged tip portion extends from the cylindrical section and is insertable into the orifice in the body.

The device of the present invention may be of a variety of sizes and can be flexible or relatively rigid. It can be fabricated of any of a number of materials including, of course, moldable non-toxic plastics.

The device is so constructed that the enlarged portion may be inserted into the orifice. The flaring tip portion is of a slightly larger diameter than the diameter of the ureter, colon or ileum. These portions of the human body are quite flexible and when the enlarged tip of the device is delicately pressed into the stoma or orifice, these organs will yield around their openings to accommodate the tip and then resiliently return to an orifice of the original size extending around the rear of the tip and gripping the device. This provides a complete and very dependable seal as well as the holding means.

The other end of the device is provided with means in the form of a groove, recess or the like to accommodate a unique disposable bag. It will thus be understood that a relatively inexpensive completely operable device is presented for use after ostomy surgery which requires no adhesives, no straps, and in fact, no fastening means independent of the structure itself.

BRIEF DESCRIPTION OF THE DRAWINGS

The drawings illustrate a preferred embodiment of the present invention and are not at all to be construed as a limitation on the scope thereof. In the drawings.

DETAILED DESCRIPTION OF THE INVENTION

Figure 1:
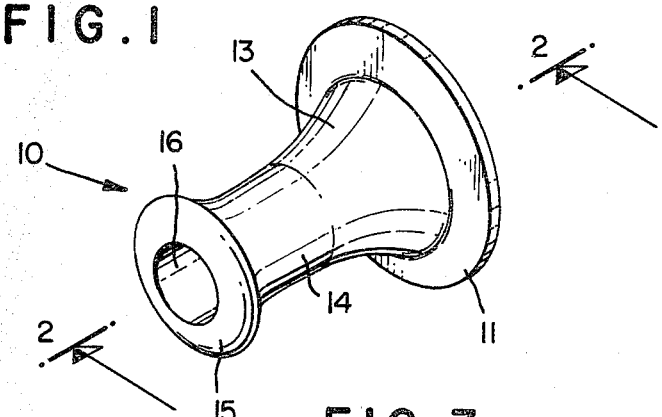
FIG. 1 is a perspective view of the medical device of the present invention.

The device 10 of the present invention is preferably made of a moldable plastic, although any suitable non-toxic material may be used. The device 10 is provided with an annular externally enlarged solid base portion 11 which, as shown, is preferably cylindrical in shape although, of course, any suitable shape may be utilized. The enlarged portion 11 may either present a flat surface around the perimeter, or as shown in the preferred embodiment, provide a groove 12 around the perimeter for the purposes hereinafter set forth.

Extending from the base 11 is an integral annular uniformly extending solid tapering section 13 and an annular uniformly extending solid relatively cylindrical section 14 at the narrower end of the tapered section 13. The surface of these portions of the device 10 are smooth and unabrasive.

Figure 2:
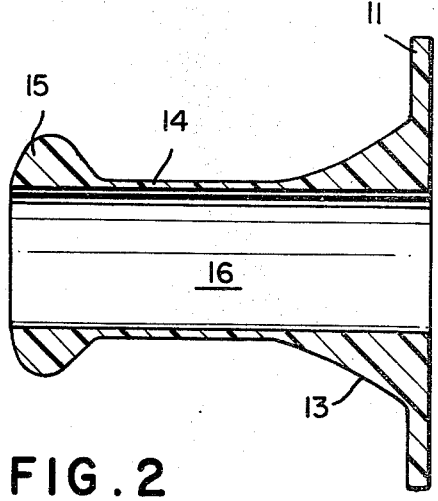
FIG. 2 is a section taken along the lines 2—2 of FIG. 1.
Figure 4:
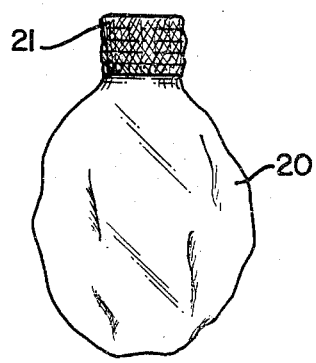
FIG. 4 is a perspective view of a unique disposable bag for use with the medical device of the present invention.
Figure 5:
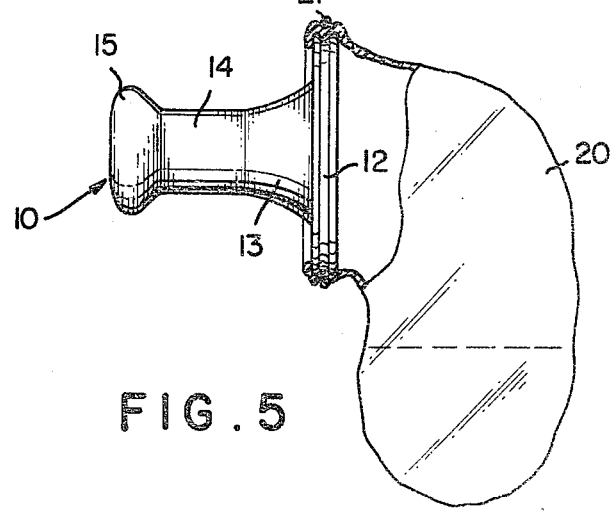
FIG. 5 is a perspective view of the device of the present invention assembled with the collection bag attached to the base.

Extending from the cylindrical section 14 is an annular externally enlarged solid uniformly extending flared tip or forward section 15 which, as shown, forms a shoulder for the purposes hereinafter set forth. This shoulder is also preferably completely smooth and without any abrasive or resisting surface characteristics. Extending through the entire integral and unitary member 10 is an opening 16, of constant and uniform diameter as shown in FIG. 2. This opening makes the otherwise solid device 10 tubular in nature and permits the passage of material from the tip 15 through the base member 11. In this regard, all internal and external surfaces of the device uniformly extend and are smooth, as shown in FIG. 2.

Figure 3:
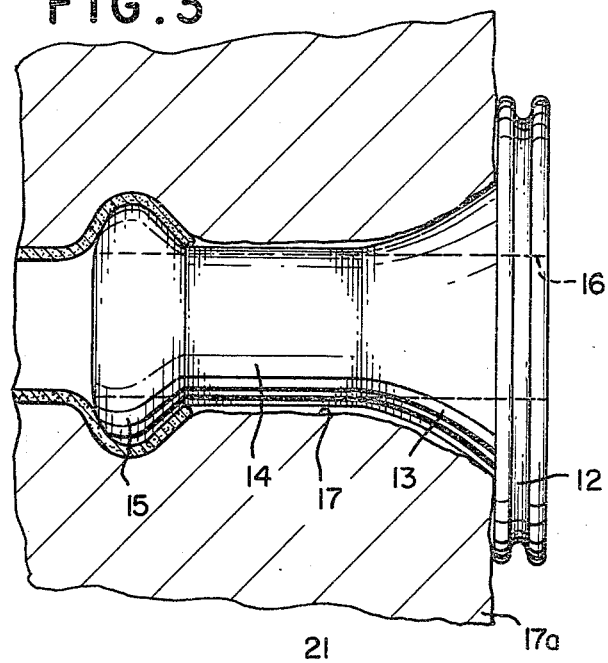
FIG. 3 is a side view showing the device partially in dotted lines inserted into the stoma and the opening in the skin of the wearer.

As shown in FIG. 3, the device 10 is inserted into a stoma or orifice in the ureter, colon or ileum 17 which is created after ostomy surgery. To insert the device of this present invention in functioning position, the tip or shoulder portion 15 is gently pressed into the orifice. As shown, the shoulder 15 is of a larger diameter than the diameter of the orifice of the ureter, colon or ileum 17. As a consequence, when the device 10 has been inserted through the orifice, the resilient organ surrounding the orifice will return into normal position to present an orifice of unextended original size and thereby surround the tip or shoulder 15 of the device 10 in the manner shown in FIG. 3. The skin 17A of the wearer also has an opening surrounding the rearward portion of the device 10 noted to accomodate the device in the body of the wearer.

There are no adhesives utilized nor any straps required to maintain the device of the present invention in its appropriate position to permit the passage of body waste materials. If desired, a seal or seals (not shown) may be placed around the inwardly disposed side of the shoulder 15 to add additional sealing characteristics, although usually such seals are not required in view of the construction and efficiency of the device 10. Thus, when the device is placed in position, it will remain there without the requirements for any further support.

It is possible, of course, to utilize the device 15 as a removable unit by simply lubricating the tip or shoulder 15 with a jelly-like substance and inserting it into the stoma from which it can be easily and gently removed without any excessive pressure. However, it is to be understood that the device itself can be permanently implanted by the surgeon at the time of the ostomy surgery and for this purpose the device would be made out of a non-toxic inert material. The unit 10 may, of course, be flexible to an extent or relatively rigid and of varying sizes and specific construction, depending upon the type of surgery and the size and shape of the stoma or orifice in the body.

The present invention contemplates the provision of a disposable bag 20, particularly adapted to contain excreted body wastes passing through the medical device 10 from the body organs. This bag is preferably of a flexible plastic material which is provided with an elastic means 21 around and forming the mouth 22 of the bag itself. It will be understood that this disposable bag may be inserted in the groove or recess 12 provided in the base portion 11. The bag, however, may also be used to enwrap the base portion 11 when no grooves or recesses are provided and only a flat surface is shown. The disposable bag of the present invention may be applied and removed with facility because of the expandable nature of the mouth portion thereof.

The flaring tip or shoulder 15 of the device 10 is shown preferably as extending at the outermost portion of the device. It is to be understood, however, that it is well within the purview of the invention to provide a shoulder or collar portion inwardly of the terminus of the device if such construction is desired.

While the invention has been described in substantial detail in order to facilitate an understanding thereof by those skilled in the art, it is to be understood that variations and modifications may be made without departing from the spirit of the invention as defined in the appended claims.

I claim:

1. Medical by-pass tubular device for insertion into a surgically created orifice in a body organ comprising:
    an annular externally enlarged solid base portion at one end of the tubular device having a perimeter provided with an external circumferential groove adapted to receive a disposable bag removably secured to the base portion thereat for receiving and containing body wastes excreted through the tubular device,
    an annular externally enlarged relatively rigid solid shoulder portion at the other end of the tubular device comprising a uniformly extending externally smooth surface flared tip adapted to be inserted into said orifice whereby the organ surrounding said orifice will enwrap such shoulder portion at said flared tip,
    an annular uniformly extending externally smooth surface solid substantially cylindrical portion, and
    an annular uniformly extending externally smooth surface solid tapered portion,
    said substantially cylindrical portion being disposed between said shoulder portion and said tapered portion and in turn said tapered portion being disposed between said substantially cylindrical portion and said base portion, and
    the tubular device being integral and unitary as well as relatively rigid and having a smooth surface tubular flow path opening of substantially constant and uniform diameter extending from the base portion of the flared tip at the shoulder portion and internally completely therethrough from said one end to said other end thereof.

2. Device according to claim 1 wherein the base, shoulder, tapered and cylindrical portions are of non-toxic relatively smooth surface plastic material.

3. Device according to claim 1 including a disposable bag removably secured to the base portion.

* * * * *